United States Patent [19]

Rostami et al.

[11] Patent Number: 5,998,572
[45] Date of Patent: Dec. 7, 1999

[54] METHODS AND DEVICES FOR CONTROLLING THE OXIDATION OF A HYDROCARBON TO AN ACID BY REGULATING TEMPERATURE/ CONVERSION RELATIONSHIP IN MULTI-STAGE ARRANGEMENTS

[75] Inventors: Ader M. Rostami, Bainbridge Island; Mark W. Dassel, Indianola, both of Wash.; Eustathios Vassiliou, Newark, Del.; David C. DeCoster, Buckley, Wash.

[73] Assignee: RPC Inc., Atlanta, Ga.

[21] Appl. No.: 09/076,753

[22] Filed: May 12, 1998

Related U.S. Application Data

[62] Division of application No. 08/859,890, May 21, 1997, Pat. No. 5,817,868.
[60] Provisional application No. 60/031,310, Nov. 12, 1996.
[51] Int. Cl.$^6$ .......................... C08G 73/00; C07C 51/00
[52] U.S. Cl. .......................... 528/322; 528/170; 528/172; 528/173; 528/176; 528/179; 528/183; 528/220; 528/229; 528/272; 528/274; 528/332; 528/335; 528/336; 528/345; 528/350; 528/351; 528/353; 562/413; 562/421; 562/509; 562/523; 562/542; 562/543
[58] Field of Search ........................ 528/272, 274, 528/322, 353, 332, 336, 335, 345, 350, 351, 170, 172, 173, 176, 179, 183, 220, 229; 562/413, 542, 509, 543, 523, 421

[56] References Cited

U.S. PATENT DOCUMENTS

| | | |
|---|---|---|
| 1,121,532 | 12/1914 | Newberry . |
| 2,014,044 | 9/1935 | Haswell ........................ 75/17 |
| 2,223,493 | 12/1940 | Loder ........................ 260/537 |
| 2,223,494 | 12/1940 | Loder ........................ 260/586 |
| 2,301,240 | 11/1942 | Baumann et al. ............ 183/115 |
| 2,439,513 | 4/1948 | Hamblet et al. ............ 260/533 |
| 2,557,282 | 6/1951 | Hamblet et al. ............ 260/533 |
| 2,565,087 | 8/1951 | Porter et al. ............... 260/631 |
| 2,980,523 | 4/1961 | Dille et al. ................. 48/215 |
| 3,161,603 | 12/1964 | Leyshon et al. ............. 252/413 |
| 3,231,608 | 1/1966 | Kollar ....................... 260/533 |
| 3,234,271 | 2/1966 | Barker et al. ............... 260/531 |
| 3,290,369 | 12/1966 | Bonfield et al. ............. 260/537 |
| 3,361,806 | 1/1968 | Lidov ....................... 260/531 |
| 3,515,751 | 6/1970 | Oberster et al. ............ 260/533 |
| 3,530,185 | 9/1970 | Pugi ......................... 260/586 |
| 3,613,333 | 10/1971 | Gardenier .................. 55/89 |
| 3,677,696 | 7/1972 | Bryk et al. ................. 23/2 |
| 3,839,435 | 10/1974 | Shigeyasu et al. .......... 260/524 R |
| 3,928,005 | 12/1975 | Laslo ........................ 55/73 |
| 3,932,513 | 1/1976 | Russell ...................... 260/586 |
| 3,946,076 | 3/1976 | Paasen et al. ............... 260/586 |
| 3,957,876 | 5/1976 | Rapoport et al. ............ 260/586 |
| 3,987,100 | 10/1976 | Barnette et al. ............. 260/586 |
| 3,987,808 | 10/1976 | Carbonell et al. ........... 137/3 |
| 4,025,498 | 5/1977 | Buss et al. ................. 260/95 A |
| 4,039,304 | 8/1977 | Bechthold et al. ........... 55/10 |
| 4,055,600 | 10/1977 | Langley et al. ............. 260/586 |
| 4,065,527 | 12/1977 | Graber ...................... 261/79 A |
| 4,308,037 | 12/1981 | Meissner et al. ............ 55/10 |
| 4,361,965 | 12/1982 | Goumondy et al. .......... 34/57 |
| 4,370,304 | 1/1983 | Hendriks et al. ............ 422/224 |
| 4,394,139 | 7/1983 | Board ........................ 55/20 |
| 4,419,184 | 12/1983 | Backlund ................... 162/49 |
| 4,423,018 | 12/1983 | Lester, Jr. et al. ........... 423/243 |
| 5,061,453 | 10/1991 | Krippl et al. ............... 422/106 |
| 5,104,492 | 4/1992 | King et al. ................. 203/15 |
| 5,123,936 | 6/1992 | Stone et al. ................. 55/8 |
| 5,170,727 | 12/1992 | Nielsen ..................... 110/346 |
| 5,221,800 | 6/1993 | Park et al. .................. 562/543 |
| 5,244,603 | 9/1993 | Davis ....................... 261/87 |
| 5,270,019 | 12/1993 | Melton et al. .............. 422/234 |
| 5,271,904 | 12/1993 | Esposito et al. ............ 422/105 |
| 5,286,458 | 2/1994 | Yang et al. ................. 422/168 |
| 5,294,378 | 3/1994 | Succi et al. ................ 261/130 |
| 5,312,567 | 5/1994 | Kozma et al. .............. 261/87 |
| 5,321,157 | 6/1994 | Kollar ....................... 562/543 |
| 5,374,767 | 12/1994 | Drinkard et al. ............ 560/193 |
| 5,396,850 | 3/1995 | Conochie et al. ........... 110/346 |
| 5,399,750 | 3/1995 | Brun et al. ................. 562/553 |

(List continued on next page.)

FOREIGN PATENT DOCUMENTS

| | | |
|---|---|---|
| 439 007 A2 | 7/1991 | European Pat. Off. . |
| 729 084 A1 | 8/1996 | European Pat. Off. . |
| 729 085 A1 | 8/1996 | European Pat. Off. . |
| 751 105 A2 | 1/1997 | European Pat. Off. . |
| 2 722 783 A1 | 1/1996 | France . |
| 4426132 A1 | 1/1996 | Germany . |
| 4427474 A1 | 2/1996 | Germany . |
| 48-003815 | 2/1973 | Japan . |
| 415172 | 8/1934 | United Kingdom . |
| 738808 | 10/1955 | United Kingdom . |
| 864106 | 3/1961 | United Kingdom . |
| 1143213 | 2/1969 | United Kingdom . |
| WO 96/03365 | 2/1996 | WIPO . |
| WO 96/40610 | 12/1996 | WIPO . |

OTHER PUBLICATIONS

Lewis, Hawley's Condensed Chemical Dictionary, 12$^{th}$ ed., 1993, pp. 7, 336, and 1076. The Month in the Date of Publication is not Available.

E. Sorribes et al., "Formación de neuvas fases en el proceso de obtención de ácido adípico: causas y efectos que provocan," *Rev. R. Acad. Cienc. Exactas, Fis. Nat. Madrid* (1987), 81 (1), 233–5 (+ English language translation). The Month in the Date of Publication is not Available.

*Primary Examiner*—P. Hampton-Hightower
*Attorney, Agent, or Firm*—Seed and Berry LLP

[57] ABSTRACT

Methods and devices for controlling the oxidation of a hydrocarbon to an acid by regulating the temperature hold-up time, and conversion in consecutive reaction zones. The temperature in the consecutive reaction zones progressively decreases, while the hold-up time increases. Preferably, the conversion also increases. One of the major advantages of the methods and devices of the present invention is that an outstanding balance between productivity and selectivity/yield of the desired acid may be achieved. In this respect high yields and selectivities may be obtained without sacrificing productivity.

12 Claims, 1 Drawing Sheet

U.S. PATENT DOCUMENTS

| | | | |
|---|---|---|---|
| 5,463,119 | 10/1995 | Kollar | 562/543 |
| 5,502,245 | 3/1996 | Dassel et al. | 562/413 |
| 5,505,920 | 4/1996 | Kollar et al. | 423/246 |
| 5,516,423 | 5/1996 | Conoby et al. | 210/85 |
| 5,558,842 | 9/1996 | Vassiliou et al. | 422/108 |
| 5,580,531 | 12/1996 | Vassiliou et al. | 422/108 |
| 5,654,475 | 8/1997 | Vassiliou et al. | 562/413 |
| 5,801,273 | 9/1998 | Vassiliou et al. | 562/413 |
| 5,801,282 | 9/1998 | Dassel et al. | 562/413 |
| 5,824,819 | 10/1998 | Dassel et al. | 562/529 |
| 5,883,292 | 3/1999 | Dassel et al. | 562/413 |
| 5,922,908 | 7/1999 | Dassel et al. | 562/542 |

METHODS AND DEVICES FOR CONTROLLING THE OXIDATION OF A HYDROCARBON TO AN ACID BY REGULATING TEMPERATURE/ CONVERSION RELATIONSHIP IN MULTI-STAGE ARRANGEMENTS

CROSS REFERENCE TO RELATED APPLICATIONS

This application is a divisional of U.S. application Ser. No. 08/859,890, filed May 21, 1997 now U.S. Pat. No. 5,817,868; which claims priority from U.S. Provisional Application No. 60/031,310, filed Nov. 12, 1996 now abandoned, where said applications are incorporated herein by reference in their entireties.

TECHNICAL FIELD

This invention relates to methods and devices for controlling the oxidation of hydrocarbons, such as cyclohexane or xylenes for example to the respective acids, with a gas containing an oxidant, preferably oxygen, for improving the selectivity and/or yield.

BACKGROUND OF THE INVENTION

There is a plethora of references (both patents and literature articles) dealing with the formation of intermediate oxidation products, such as diacids, for example, one of the most important being adipic acid. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process", the "Boric Acid Process," and the "Direct Synthesis Process, " which involves direct oxidation of cyclohexane to adipic acid with oxygen in the presence of solvents, catalysts, and initiators or promoters.

Initiators or promoters are presently being used to shorten considerably an induction period at the beginning of the reaction. Accepted explanations, which have been given regarding the role of the initiators or promoters, involve oxidation of the catalyst, which is usually cobaltous ions to cobaltic ions.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis Process, a mixture of two liquid phases is present at ambient temperature, along with a solid phase mainly consisting of adipic acid. The two liquid phases have been called the "Polar Phase " and the "Non-Polar " phase. However, no attention has been paid so far to the importance of the two phases, except for separating the adipic acid from the "Polar Phase " and recycling these phases to the reactor partially or totally with or without further treatment. Further, no attention has been paid to the behavior of catalyst, such as solubility, for example, during reaction conditions.

It is also important to note that most, if not all, studies on the Direct Synthesis Process have been conducted in a batch mode, literally or for all practical purposes.

There is a plethora of references dealing with oxidation of organic compounds to produce acids, such as, for example, adipic acid, benzoic acid, phthalic acid, isophthalic acid, terephthalic acid, etc.

The following references, among the plethora of others, may be considered as representative of oxidation processes relative to the preparation of diacids, and especially adipic acid.

U.S. Pat. No. 5,463,119 (Kollar) discloses a process for the oxidative preparation of $C_5$–$C_8$ aliphatic dibasic acids by
  (1) reacting,
    (a) at least one saturated cycloaliphatic hydrocarbon having from 5 to 8 ring carbon atoms in the liquid phase and
    (b) an excess of oxygen gas or an oxygen-containing gas in the presence of
    (c) a solvent comprising an organic acid containing only primary and/or secondary hydrogen atoms and
    (d) at least about 0.002 mole per 1000 grams of reaction mixture of a polyvalent heavy metal catalyst;
  (2) removing the aliphatic dibasic acid; and
  (3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g., a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of $C_5$–$C_8$ aliphatic dibasic acids through oxidation of corresponding saturated cycloaliphatic hydrocarbons by
  (1) reacting, at a cycloaliphatic hydrocarbon conversion level of between about 7% and about 30%.
    (a) at least one saturated cycloaliphatic hydrocarbon having from 5 to 8 ring carbon atoms in the liquid phase and
    (b) an excess of oxygen gas or an oxygen containing gas mixture in the presence of
    (c) less than 1.5 moles of a solvent per mole of cycloaliphatic hydrocarbon (a), wherein said solvent comprises an organic acid containing only primary and/or secondary hydrogen atoms and
    (d) at least about 0.002 mole per 1000 grams of reaction mixture of a polyvalent heavy metal catalyst; and
  (2) isolating the $C_5$–$C_8$ aliphatic dibasic acid.

U.S. Pat. No. 5,221,800 (Park et al.) discloses a process for the manufacture of adipic acid is disclosed. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° C. to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Patent DE 44 26 132 A 1 (Kysela et al.) discloses a method for dehydration of process acetic acid from the liquid-phase oxidation of cyclohexane with air, in the presence of cobalt salt as a catalyst after separation of the adipic acid by filtration and the cyclohexane phase by phase separation, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than about 0.3 to 0.7 wt %.

PCT Demand International publication WO 96/03365 (Costantini et al.) discloses a method of recycling a cobalt-containing catalyst in a reaction involving the direct oxidation of cyclohexane into adipic acid using an oxygen containing gas. The method is characterized in that the reaction mixture, obtained in a preceding stage where the cyclohexane was oxidized into adipic acid, of which at least part of the intermediate oxidation products, such as cyclohexanol and cyclohexanone, the carboxylic acid and water has been separated and of which at least part of the adipic acid formed has been recovered by crystallization, undergoes at least one extraction operation using at least one co-solvent or a mixture comprising a co-solvent and a carboxylic acid. The method is also characterized by the separation of a mixture containing at least part of the cobalt catalyst, part of the carboxylic acid and optionally residual quantities of other compounds and a solution containing the co-solvent and at least part of the glutaric and succinic acids formed during the oxidation reaction, and the carboxylic acid.

None of the above references, or any other references known to the inventors disclose, suggest or imply, singly or in combination, oxidation of cyclic hydrocarbons to dibasic acids in multiple stages of temperature/conversion, subject to the intricate and critical controls and requirements of the instant invention as described and claimed.

Our U.S. Pat. Nos. 5,580,531, 5,558,842, 5,502,245, and our co-pending applications 08/477,195 (filed Jun. 07, 1995), 08/587,967 (filed Jan. 17, 1996), and 08/620,974 (filed Mar. 251,996), all of which are incorporated herein by reference, describe methods and apparatuses relative to controlling reactions in atomized liquids.

Our co-pending application, Docket No. T-603, of Mark W. Dassel, Eustathios Vassiliou. David C. DeCoster, Ader M. Rostami, and Sharon M. Aldrich, titled "Methods and Devices for Controlling the Reaction Rate of a Hydrocarbon to an Acid by Making Phase-related Adjustments", filed on Mar. 6, 1997, and having a Ser. No. 08/812,847, is also incorporated herein by reference.

Our co-pending application, Docket No. T-701, of Mark W. Dassel, David C. DeCoster, Ader M. Rostami, Sharon M. Aldrich, and Eustathios Vassiliou, titled "Methods and Devices for Preparing Dibasic Acids", filed on Mar. 27, 1997, and having a Ser. No. 08/824,992 is also incorporated herein by reference.

All of the following patent applications, which were filed simultaneously with the present application are also incorporated herein by reference:

Docket U.S. patent application Ser. No. 08/889,985 of Eustathios Vassiliou, Mark W. Dassel, David C. DeCoster, Ader M. Rostami, and Sharon M. Aldrich, titled "Methods and Devices for Controlling the Reaction Rate of a Hydrocarbon to an Intermediate Oxidation Product by Pressure Drop Adjustments", Docket No. U.S. patent application Sr. No. 08/862,281 of Mark W. Dassel, Eustathios Vassiliou, David C. DeCoster, Ader M. Rostami, and Sharon M. Aldrich, titled "Methods and Devices for Controlling the Reaction Rate of a Hydrocarbon to an Intermediate Oxidation Product by Monitoring Flow of Incoming and Outcoming Gases";

Docket U.S. patent application Ser. No. 08/861,180 of David C. DeCoster, Ader M. Rostami, Mark W. Dassel, and Eustathios Vassiliou, titled "Methods and Devices for Controlling the Oxidation Rate of a Hydrocarbon by Adjusting the Ratio of the Hydrocarbon to a Rate-Modulator":

Docket U.S. patent application Ser. No. 08/861,176 of Mark W. Dassel, Eustathios Vassiliou, David C. DeCoster, and Ader M. Rostami, titled "Methods of Preparing an Intermediate Oxidation Product from a hydrocarbon by Utilizing an Activated Initiator"; and Docket U.S. patent application Ser. No. 08/861,210 of Eustathios Vassiliou, Ader M. Rostami, David C. DeCoster, and Mark W. Dassel, titled "Pseudo-Plug-Flow Reactor."

SUMMARY OF THE INVENTION

As aforementioned, this invention relates to methods of making dibasic acids by oxidizing a hydrocarbon with a gas containing an oxidant, preferably oxygen. More particularly, it relates to a method of oxidizing a hydrocarbon to an acid with a gaseous oxidant comprising the steps of:

(a) reacting the hydrocarbon with the oxidant at a first oxidation rate and at a first temperature in a first reaction zone, the first reaction zone being characterized by a first hold-up time;

(b) continuing reacting the hydrocarbon with the gaseous oxidant at a second oxidation rate and at a second temperature in a second reaction zone, the second reaction zone being characterized by a second hold-up time, the second temperature being lower than the first temperature, the first hold-up time to the second hold-up time being at a ratio lower than 1.

Preferably, reacting the hydrocarbon is continued in step (a) until the hydrocarbon has attained a first conversion within a desired first conversion range and/or reacting the hydrocarbon is continued in step (b) until the hydrocarbon has attained a second conversion within a desired second conversion range. More preferably, the first conversion to the second conversion are at a ratio lower than 1.

This invention also pertains to a method as described above, further comprising n−2 additional steps of continuing reacting the hydrocarbon with the gaseous oxidant at an nth oxidation rate in an nth reaction zone, the nth reaction zone being characterized by an nth hold-up time, at an nth temperature, the nth temperature being lower than a respective n−1 temperature in a respective n−1 reaction zone characterized by an n−1 hold-up time, the n−1 hold-up time to the nth hold-up time being at a ratio lower than 1, n being an integer greater than 2, and preferably 3–5. Reacting the hydrocarbon is preferably continued until the hydrocarbon has attained an n−1 conversion in the n−1 reaction zone and an nth conversion in an nth reaction zone.

Every step and its previous step have preferably a similar relationship and or trend as the second and first steps or the nth and n−1 steps with respect to reaction rates, hold up times, temperatures, conversions, combinations thereof, and the like.

In the case of two reaction zones, the desired first conversion range is preferably 0.1% to 20%, and more preferably 1% to 10%, while the second desired conversion range is preferably 1% to 80%, and more preferably 5% to 50%, based on the total conversion.

The second temperature is preferably 2° C. to 50° C. lower than the first temperature, and more preferably 10° C. to 30° C.

This method is particularly applicable to the case wherein the hydrocarbon comprises cyclohexane, the gaseous oxidant comprises oxygen, and the acid comprises adipic acid.

In another example, the hydrocarbon comprises a species selected from a group consisting of o-xylene, m-xylene, p-xylene, and a mixture thereof, and the acid comprises a moiety selected from a group consisting of o-phthalic acid, isophthalic acid. terephthalic acid and a mixture thereof! respectively. In still another example, the hydrocarbon comprises toluene and the acid comprises benzoic acid.

The method may further comprise a step of forming a mixture containing hydrocarbon, catalyst, and initiator, and of atomizing the mixture in at least one of the reaction zones. Similarly, the mixture may be stirred and brought in contact with the oxidant, or it may be brought in contact with the oxidant in a plug flow mode.

Further, the instant invention pertains to a method, wherein the acid comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

The method may further comprise a step of spinning the polymer into fibers.

This invention also pertains to a device for oxidizing a hydrocarbon to an acid with a gaseous oxidant, the device comprising in combination an assembly of:

a first reaction chamber having a first volume;

first hydrocarbon feeding means for feeding liquids comprising a hydrocarbon into the first reaction chamber;

first gaseous oxidant feeding means for feeding gaseous oxidant into the first reaction chamber;

first temperature control means for controlling a first temperature within the first reaction chamber;

a second reaction chamber having a second volume;

a first liquid transfer means for transferring liquids from the first reaction chamber to the second reaction chamber;

second gaseous oxidant feeding means for feeding gaseous oxidant into the second reaction chamber;

second temperature control means for controlling a second temperature within the second reaction chamber;

the first volume and the second volume being adapted to accommodate a desired first hold-up time of liquids in the first reaction chamber and a desired second hold-up time in the second reaction chamber, the first hold-up time to the second hold-up time being at a ratio lower than 1.

The device may further comprise hold-up time means for controlling the hold-up times in the first reaction chamber and in the second reaction chamber to be within predetermined limits. It may also comprise conversion detection means for determining the first conversion and the second conversion. In one example, the conversion detection means are adapted to utilize chemical or physical analysis of liquids or gases for determining conversion. In another example, the conversion detection means are adapted to utilize oxidation rate in the respective reaction chamber for determining conversion.

In addition, the device may further comprise:

an n−1 reaction chamber having an n−1 volume;

an n−1 hydrocarbon feeding means for feeding liquids comprising a hydrocarbon into the n−1 reaction chamber;

an n−1 gaseous oxidant feeding means for feeding gaseous oxidant into the n−1 reaction chamber;

an n−1 temperature control means for controlling an n−1 temperature within the n−1 reaction chamber;

an nth reaction chamber having an nth volume;

an n−1 liquid transfer means for transferring liquids from the n−1 reaction chamber to the nth reaction chamber;

an nth gaseous oxidant feeding means for feeding gaseous oxidant into the nth reaction chamber;

nth temperature control means for controlling a nth temperature within the nth reaction chamber;

the n−1 volume and the nth volume being adapted to accommodate a desired n−1 hold-up time of liquids in the n−1 reaction chamber and a desired nth hold-up time in the nth reaction chamber, the n−1 hold-up time to the nth hold-Lip time being at a ratio lower than 1, n being an integer greater than 2, and preferably 3–5.

In one example, at least one of the reaction chambers is an atomization reaction chamber. However, this invention applies to any type of reaction chamber, such as stirred tank or plug flow reaction chambers, for example.

The lower conversions per stage, according to this invention, simplify the heat transfer problems as well as the design of each reaction chamber. Furthermore, they provide better energy efficiency.

BRIEF DESCRIPTION OF THE DRAWING

The reader's understanding of this invention will be enhanced by reference to the following detailed description taken in combination with the drawing figures, wherein.

DETAILED DESCRIPTION OF THE INVENTION

Figure 1:
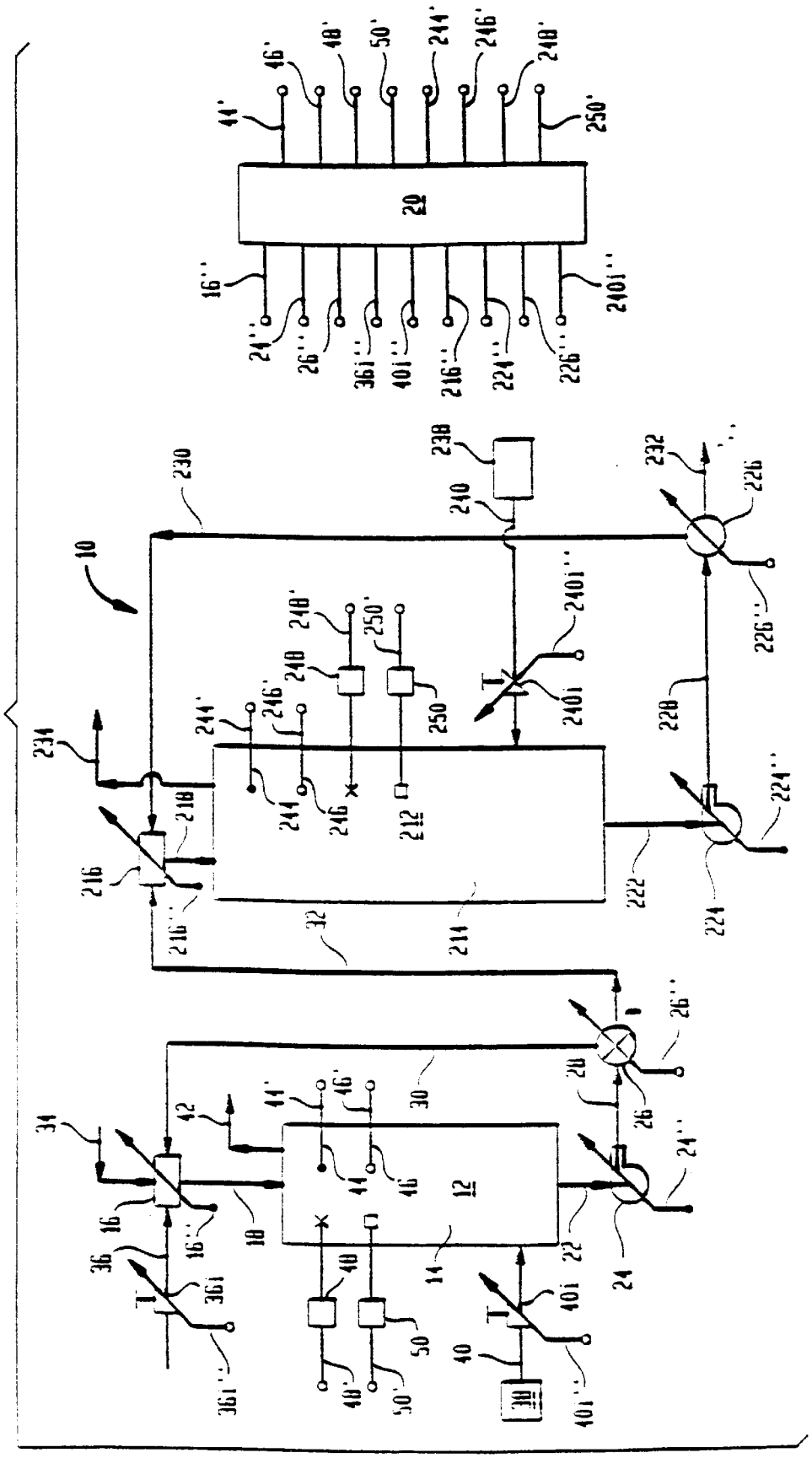
FIG. 1 illustrates schematically in the form of a block diagram a preferred multiple embodiment of the present invention, wherein a first reaction chamber operates at a first temperature, while the second reaction chamber operates at a second temperature, lower than the first temperature. The ratio of hold-up time in the first reaction chamber to the hold-up time in the second reaction chamber is lower than 1.

As mentioned earlier, this invention relates to methods of making intermediate oxidation products, such as acids, for example, by oxidizing a hydrocarbon with a gas containing an oxidant, preferably oxygen.

In addition to the formation of adipic acid, the methods of the present invention may also be applied to other diacids from the corresponding cyclic aliphatic or aromatic hydrocarbons. Examples are formation of glutaric acid from cyclopentane, formation of pimelic (heptanedioic) acid from cycloheptane, phthalic acid from oxylene, isophthalic acid from m-xylene, terephthalic acid from p-xylene, benzoic acid from toluene, and the like, for example.

High selectivity and/or high yield combined with high production rate or productivity is of utmost importance. A delicate balance between selectivity and/or yield and production rate or productivity exists, depending on the particular circumstances. If the production rate or productivity is unacceptably high, low yields may be observed. On the other hand, if the production rate or productivity is too low, even with 100% yield the process may be grossly uneconomical. This delicate balance between the selectivity and/or yield and the production rate or productivity depends on the particular circumstances. It is of utmost importance, however, to be able to control it and maintain it.

For the purposes of the instant invention the definitions provided hereinbelow apply. If definitions given in other references, differ from the ones given below, they should be taken just within the context of each particular reference. This includes also documents incorporated herein by reference.

Selectivity in the case of direct synthesis of adipic acid is defined as the molar amount of adipic acid produced divided by the sum of the molar amounts of 1 adipic acid, glutaric acid and succinic acid produced during the reaction and multiplied by 100. For direct synthesis of other acids, selectivity is defined as the molar amount of the respective acid produced divided by the sum of the molar amounts of the respective acid and all major by-products. Major by-product is defined as one which amounts to more than 1 pph (parts per hundred), molar, based on the respective acid.

Yield is defined as the molar amount of hydrocarbon corresponding to acid produced, divided by the total molar amount of hydrocarbon consumed during the reaction, and multiplied by 100.

Conversion is defined as the weight amount of hydrocarbon consumed divided by the sum of the weight amount of hydrocarbon consumed plus the weight amount of non-reacted hydrocarbon, and multiplied by 100.

Oxidation rate is defined as the molar rate at which a hydrocarbon is oxidized to acid.

Pressure drop rate is defined as the pressure drop in p.s.i. per minute in a reaction chamber, wherein any flow of matter into or out of the reaction chamber have stopped, under all other conditions remaining constant, or any equivalents of this, such as for example equal volumes of matter entering and exiting the reaction chamber, under all other conditions remaining constant.

Production rate is defined as the weight production of acid per unit time.

Productivity is defined as the weight production of acid per unit time and per unit volume of reaction zone.

Input and output lines refer to signal lines between a controller and different elements or devices. Both "input" and "output" are considered with regard to the controller.

Inlet and outlet lines refer to lines transferring fluids, which enter or exit different elements, such as reaction chambers for example, respectively.

Hold-up time is defined the time that it would take for a reaction chamber or a reaction zone to be emptied at a specified flow rate, with nothing being added to the reaction chamber.

A preferred multiple embodiment of this invention is illustrated in FIG. 1. By the expression "multiple embodiment" it is meant that a number of combinations of elements may be utilized without the need of other elements, also shown. The not-utilized elements in such a case, however, may be used in other combinations to satisfy the same or similar needs and/or functions, as it will be explained in more detail hereinbelow.

In FIG. 1, there is depicted a device or continuous reactor system 10 comprising a first reaction chamber 12, which has a first volume, and a second reaction chamber 212, which has a second volume. The first reaction chamber 12 encloses a first reaction zone 14, and the second reaction chamber 212 encloses a second reaction zone 214. A first hydrocarbon feeding means 16 is connected to the reaction chamber 12 through first hydrocarbon feed line 18. The first hydrocarbon feeding means 16 may be a pre-mixing vessel and/or a heat exchanger, which heat exchanger is capable to regulate the temperature of the liquids containing hydrocarbon and entering the first reaction chamber 12 through first hydrocarbon feed or inlet line 18. The hydrocarbon feeding means 16 is controlled by a controller 20, preferably computerized, through output line 16". Output line 16" is shown only partially at the controller 20 and at the control point of the first hydrocarbon feeding means 16, for purposes of clarity. All other lines connecting the inputs and outputs of the controller 20 and different points of control of respective elements are treated in a similar manner, also for purposes of clarity. The controller 20 may also control the temperature of the first reaction chamber 12 by controlling other means (not shown) well known to the art, such as heating or cooling devices inside or outside the reaction chamber 12.

A first liquid outlet line 22 connects the first reaction chamber 12 with a first liquid transfer means, such as a first pump 24, for example. The first pump 24 is also controlled by the controller 20 through output line 24". The first pump 24 is in turn connected to a first three way valve 26 through line 28. The three way valve 26, which is also controlled by the controller 20 through output line 26", splits the liquids into two streams, one to first recirculation line 30 and one to first transfer line 32. Flow meters in one or more of lines 28, 30, and 32 connected to respective inputs of the controller 20, which serve as monitors of flow values to be provided to the controller 20, and their respective input lines are not shown for purposes of clarity.

The first hydrocarbon feeding means 16 are fed by first recirculation line 30, final recirculation line 34, and new raw material line 36. The final recirculation line 34 brings back to the first reaction chamber 12 materials after removal of products and by-products from a separator (not shown for purposes of clarity) similar to the one shown in FIG. 1 of U.S. Pat. No. 5,502,245 by numeral 15. This separator may include heaters, evaporators, distillation columns, filters, crystallizers, and other equipment, well known to the art.

Flow through the new raw material line 36 is regulated by valve 36i". which in turn is controlled by controller 20 through line 36i".

Gaseous oxidant feeding means 38 are connected to the first reaction chamber 12 through first oxidant feed or inlet line 40. The flow of gaseous oxidant through first oxidant feed or inlet line 40 is regulated by valve 40i, which valve is in turn controlled by the controller 20 through output line 40i". The gaseous oxidant feeding means may be a tank of oxidant, such as air or a mixture of oxygen and inert gas for example, such as nitrogen for example, or it may by a compressor, or any other reservoir or device, well known to the art, which is capable of providing oxidant to the first reaction chamber 12. Devices such as thermometers, flow meters for example, etc., connected to line 40 in order to give temperature, flow and other information to the controller 20 through respective input lines are not shown for purposes of clarity.

A first gas exit line 42 is also connected to the first reaction chamber 12. This line is also preferably provided with flow regulating valve(s), flow meter(s), temperature monitor(s), oxygen content monitor(s), carbon dioxide and monoxide monitor(s), etc., connected to the controller 20 through respective output and input lines. These devices and lines are not shown for purposes of clarity, but they are very well known to the art.

The first reaction chamber 12 is also provided with a temperature monitor 44, a pressure monitor 46, an oxygen analyzer 48, and a chemical analyzer 50, which is preferably a chromatographic instrument. These devices are connected to the controller 20 through input lines 44', 46', 48', and 50', respectively. The temperature monitor 44 and the pressure monitor 46 are in most cases necessary, while the oxygen analyzer 48 and the chemical analyzer 48 may be optional, since the main purpose of the analyzers, according to this embodiment, is to give information to the controller 20 for calculation of the conversion of hydrocarbon in the reaction chamber 12. Other information may become available, from which the controller may calculate the conversion of the hydrocarbon to acid. Such information may become available, for example through devices as described and claimed in our co-pending application Docket No. T-604, and our co-pending application Docket No. T-605, both referred to earlier.

The first transfer line 32 is connected to a second hydrocarbon feeding means 216, which feeds the second reaction chamber 212 with liquids containing partially reacted hydrocarbon, through a second hydrocarbon feed or inlet line 218. The second hydrocarbon feeding means 216 is preferably similar to the first hydrocarbon feeding means 16.

The second reaction chamber 212 encloses a second reaction zone 214. The second hydrocarbon feeding means 216 may be a pre-mixing vessel and/or a heat exchanger, which heat exchanger is capable to regulate the temperature of the liquids containing hydrocarbon and entering the second reaction chamber 212 through the second hydrocarbon feed or inlet line 218. The hydrocarbon feeding means 216 is controlled by the controller 20 through output line 216". Output line 216" is shown only partially at the controller 20 and at the control point of the second hydrocarbon feeding means 216, for purposes of clarity. All other lines connecting the inputs and outputs of the controller 20 and different points of control of respective elements are treated in a similar manner, also for purposes of clarity. The controller 20 may also control the temperature of the second reaction chamber 212 by controlling other means (not shown) well known to the art, such as heating or cooling devices inside or outside the reaction chamber 212.

A second liquid outlet line 222 connects the second reaction chamber 212 with a second liquid transfer means such as a second pump 224, for example. The second pump 224 is also controlled by the controller 20 through output line 224". The second pump 224 is in turn connected to a second three way valve 226 through line 228. The three way valve 226, which is also controlled by the controller 20 through output line 226", splits the liquids into two streams, one to second recirculation line 230 and one to second transfer line 232. Flow meters in one or more of lines 228, 230, and 232 connected to respective inputs of the controller 20, which serve as monitors of flow values to be provided to the controller 20, and their respective input lines are not shown for purposes of clarity.

The second hydrocarbon feeding means 216 are fed by second recirculation line 230, and first transfer line 32. The second transfer line 232 transfers materials for removal of products and by-products to a separator (not shown for purposes of clarity) similar to the one shown in FIG. 1 of U.S. Pat. No. 5,502,245 by numeral 15. This separator may include heaters, evaporators, distillation columns, filters, crystallizers, and other equipment, well known to the art.

In other preferred embodiments, where there is one or more reaction chambers (not shown) following the reaction chamber 212 and before the above mentioned separator, the second transfer line 232 is connected to a third hydrocarbon feeding means (not shown) in a similar manner that the first transfer line 32 is connected to the second hydrocarbon feeding means 216. All reaction chambers following the second reaction chamber 212 are similar to the reaction chamber 212. connected to similar devices in a similar manner.

Gaseous oxidant feeding means 238 are connected to the second reaction chamber 212 through second oxidant feed or inlet line 240. The flow of gaseous oxidant through second oxidant feed or inlet line 240 is regulated by valve 240$i$, which valve is in turn controlled by the controller 20 through output line 240$i$". The gaseous oxidant feeding means may be a tank of oxidant, such as air or a mixture of oxygen and inert gas for example, such as nitrogen for example, or it may by a compressor, or any other reservoir or device, well known to the art, which is capable of providing oxidant to the second reaction chamber 212. Devices such as thermometers, flow meters for example, etc., connected to line 240 in order to give temperature, flow and other information to the controller 20 through respective input lines are not shown for purposes of clarity.

A second gas exit line 242 is also connected to the second reaction chamber 212. This line is also preferably provided with flow regulating valve, flow meter(s), temperature monitor(s), oxygen content monitor(s), carbon dioxide and monoxide monitor(s), etc., connected to the controller 20 through respective output and input lines. These devices and lines are not shown for purposes of clarity, but they are very well known to the art.

The second reaction chamber 212 is also provided with a temperature monitor 244, a pressure monitor 246, an oxygen analyzer 248, and a chemical analyzer 250, which is preferably a chromatographic instrument. These devices are connected to the controller 20 through input lines 244', 246', 248' and 250', respectively. The temperature monitor 244 and the pressure monitor 246 are in most cases necessary, while the oxygen analyzer 248 and the chemical analyzer 248 may be optional, since the main purpose of the analyzers, according to this embodiment, is to give information to the controller 20 for calculation of the conversion of hydrocarbon in the reaction chamber 212. Other information may become available, from which the controller may calculate the conversion of the hydrocarbon to acid. As aforementioned, such information may become available, for example through devices as described and claimed in our co-pending U.S. patent application Ser. No. 08/859,985and our co-pending U.S. patent application Ser. No. 08/861,281, referred to earlier.

In operation of the above embodiments, liquids containing a hydrocarbon, such as cyclohexane for example, are introduced into the first hydrocarbon feeding means 16 through new raw material feeding line 36. The flow of liquids through line 36 is regulated by valve 36$i$", which valve is in turn controlled by the controller 20. In addition to the hydrocarbon, such as cyclohexane for example, solvents, such as acetic acid for example, catalysts, such as cobalt salts for example, initiators, such as acetaldehyde or cyclohexanone for example, promoters, and other adjuncts, may also be introduced along with the hydrocarbon. Unreacted hydrocarbon along with other desirable unreacted matter enters the first hydrocarbon feeding means 16 through the final recirculation line 34. Material from the first recirculation line 30 also enters the first hydrocarbon feeding means 16. The liquids entering the first hydrocarbon feeding means through lines 30, 34, and 36 are mixed in the feeding means 16 and they are brought to a desired temperature, so that the temperature that they attain in the reaction zone 14 of the reaction chamber 12 is a first temperature falling within a desired range, as measured by the thermocouple 44, which thermocouple gives this temperature information to the controller 20 through input line 44'. If the first temperature exceeds the desired range, the controller 20 instructs the first hydrocarbon feeding means to decrease the temperature of the liquids passing through it. If the first temperature is lower than the lower limit of the desired range, the controller 20 instructs the first hydrocarbon feeding means to increase the temperature of the liquids passing through it. As aforementioned, the controller 20 may also adjust the temperature of the reaction zone 14 through conventional cooling or heating elements (not shown) inside or outside the reaction chamber 12. Thus, the first temperature may be adjusted to fall within the desired range either by control of the first hydrocarbon feeding means 16 or by control of said heating or cooling elements. Of course, alternate ways, well known to the art, to control temperature in the reaction zone may be utilized. Such ways include, but are not limited to controllably evaporating at least partially solvents and/or volatile reactants.

The pressure in the reaction zone 14 inside the reaction chamber 12, is measured by the first pressure monitor 46 and the information received is transmitted to the controller 20, which after processing regulates valve 40$i$ through output line 40$i$' and a valve (not shown for purposes of clarity) in first gas exit line 42 in a manner to maintain the pressure in the reaction zone 14 inside the reaction chamber 12 within certain desired limits. If the pressure is too high, valve 40 may be instructed by the controller 20 to close further or the aforementioned valve in line 42 to open more or both. In contrast, if the pressure is too low, valve 40 may be instructed to open further or the aforementioned valve in line 42 to close more or both.

The preferred gaseous oxidant comprises oxygen. The oxygen monitor 48, which may be located within the reaction zone 14 or in the first gas exit line 42 (or oxygen monitors similar to the oxygen monitor 48 may be located in both positions) measures the oxygen content and transmits this information to the controller 20 through input line 48'. The controller 20 calculates the rate of oxygen depletion based on data from the oxygen monitor, as well as miscellaneous other data regarding temperature, amounts of incoming and outcoming gases and oxygen, etc., determined by methods well known to the art. From these calculations, the reaction rate may also be calculated, as well as the conversion of hydrocarbon to products and by-products. The conversion may also be measured directly by the first chemical analyzer 50, which samples liquids from the reaction zone 14, and preferably runs them through a GC or even more preferably through a GC/MS column, or through a GC column provided with an ionization detector, for determining the content of hydrocarbon in the liquids contained in the reaction zone 14. The chemical analyzer may be sampling either from the reaction zone 14 or from the first liquid outlet 22, or from any other suitable region. The information from this analysis is transmitted to the controller 20 through input line 50', where it is processed by the controller 20 in order to determine a first conversion. This processing involves information obtained by the controller 20 regarding the weight percent amount of hydrocarbon entering the first hydrocarbon feeding means 16 from the combination of lines 34 and 36 per unit of time, and the weight percent amount of hydrocarbon remaining in the reaction zone 14 within the reaction chamber 12, or exiting the reaction chamber 12 through the first liquid outlet 22 per unit of time.

Preferably, the reaction is run at substantially steady state conditions, which implies that the levels of hydrocarbon, solvents, catalysts, initiators, and other adjuncts entering the reaction chamber have been established and optimized for any particular case. However, this is not necessary. Also preferably, on average, the flow rate of liquids entering the first hydrocarbon feeding means 16 should be substantially equal to the flow rate of liquids passing through line 32 to the second hydrocarbon feeding means 216, after taking into account evaporation and reaction stoichiometry. As the first reaction chamber 12 has a first volume, the volume of the liquids in the first reaction chamber 12 cannot exceed this first volume. If the volume of the liquids in the first reaction chamber is considerably smaller than the first volume, then the flow rate of the liquids entering the reaction chamber 12 may, for a period of time, be larger than the flow rate of the liquids passing through the first transfer line 32.

According to the instant invention, it is important that the liquids remain in average in the first reaction chamber for a first hold-up time within a desired first hold-up time region. Thus, it is important to have an arrangement which is capable to make adjustments in order to attain and maintain such hold-up time conditions. For a constant volume of liquids within the reaction chamber 12, the hold-up time may be adjusted by regulating the flows of incoming liquids from lines 34 and 36, and the outcoming liquids from line 22. To increase the hold-up time, both flows, which should remain substantially equal to each other, are decreased. Similarly, to decrease the first hold-up time, both flows, which should remain substantially equal to each other, are increased.

On the other hand, if it is desired to maintain the flow rates substantially constant, the volume of the liquids in the reaction chamber is increased for increasing the first hold-up time, and the volume of the liquids in the reaction chamber is decreased for decreasing the first hold-up time.

The volume of the liquids within the first reaction chamber 12 may be increased by temporarily keeping the initial flow rate of liquids through the first transfer line 32 constant or decreased, and increasing the initial flow rate of incoming liquids through lines 34 and 36 until the desired volume of liquids has been reached within the reaction chamber 12, at which point the initial flow rates (substantially equal to each other) are re-established.

It is preferred, especially in the case of atomization reaction chambers as described in more detail in our patents and applications referenced earlier, that a first recirculation line 30 is used to recirculate part of the stream from line 28 back to the reaction chamber 12, and direct part of the stream to the second hydrocarbon feeding means 216 through the transfer line 32. This is regulated by the controller 20.

Regardless of the way the controller 20 adjusts the first hold-up time, it controls the flow rate of the incoming liquids through lines 34 and 36 to be substantially equal to the liquids being transferred through first transfer line 32. The total amount of liquid exiting the reaction chamber 12 through the first liquid outlet 22 is determined by the first pump 24 which in turn is controlled by the controller 20 through output line 24". Similarly, the amount of liquid to be recirculated through the first recirculation line 30 and the amount of liquid to be transferred to the second hydrocarbon feeding means 216 are regulated by the first three way valve 26, which is controlled by the controller 20 through line 26".

After the liquid from the first reaction chamber 12 enters the second hydrocarbon feeding means 216, where it is mixed with re-circulated liquid from second recirculation line 230, and the mixture is adjusted to have a second temperature, lower than the first temperature. In sequence, the mixture from lines 32 and 230 enters the second reaction chamber 212 into the second reaction zone 214, where it continues reacting with oxidant, preferably oxygen which is provided by the second gaseous oxidant feeding means 238 through line 240. The flow of gaseous oxidant is regulated by valve 240i, which in turn is controlled by the controller 20 through output line 240ii.

The reaction chamber 212, which encloses the reaction zone 214, is such that the hold up time in zone 214 is larger than the hold up time in the first reaction zone 14, which is enclosed by the reaction chamber 14, while the flows of incoming liquids and outgoing liquids in both reaction chambers 12, 212, and reaction zones 14, 214, respectively, arc substantially equal to each other. Thus, the ratio of first hold-up time to the second hold-up time is lower than 1.

The processing of liquids and gases in the second reaction chamber is substantially the same except that the second temperature in the second reaction zone 214 is lower than the first temperature in the first reaction zone 14, there is no recirculated liquid coming from the separator (not shown), described earlier, to the second hydrocarbon feeding means 216, and the second hold-up time is longer than the first hold-up time. In general, it is preferable that the lower the second temperature of the second reaction zone 214, the larger the second hold-up time. It is preferable that the second hold-up time is such that a second conversion falling within a desirable second conversion range is attained. This may be achieved preferably, assuming steady state conditions as discussed earlier, by adjusting either the second temperature or the second hold-up time by regulating the appropriate parameters by means of the controller 20, as discussed earlier for the first temperature and the first hold-up time. As aforementioned, the controller is preferably a computerized controller. The second temperature is preferably 2° C. to 50° C. lower than the first temperature, and more preferably 10° C. to 30° C. The desired first conversion range is preferably 0.1% to 20%, and more preferably 1% to 10%, while the second desired conversion range is preferably 1% to 80%, and more preferably 5% to 50%, based on total conversion, provided that the ratio of the first conversion to the second conversion is also lower than 1, and the ratio of the first hold-up time to the second hold-up time is lower than 1.

The liquids from the second transfer line 232 go to a separator (not shown) as described earlier. Recyclable raw materials and intermediate products return to the first hydrocarbon feeding means.

Between the second reaction chamber 212 and the separator (not shown) as described earlier, there may be one or more additional reaction chambers, in which the operational temperature become progressively lower, and the hold-up times become progressively larger as described earlier. These reaction chambers are similar to the second reaction chamber 212.

The miscellaneous reaction chambers of this invention may be of different types, such as for example atomization, stirred tank, plug flow, etc. All reaction chambers may be of the same type, or some of one type and some of other types. Further, a reaction chamber may be one unit or more than one units arranged in parallel.

One of the major advantages of the methods and devices of the present invention is that an outstanding balance between productivity and selectivity/yield of the desired acid may be achieved. In this respect high yields and selectivities may be obtained without sacrificing productivity.

Oxidations according to this invention, are non-destructive oxidations, wherein the oxidation product is different than carbon monoxide, carbon dioxide, and a mixture thereof. Of course, small amounts of these compounds may be formed along with the oxidation product, which may be one product or a mixture of products.

Examples include, but of course, are not limited to preparation of $C_5$–$C_{12}$ aliphatic dibasic acids from the corresponding saturated cycloaliphatic hydrocarbons, such as for example preparation of adipic acid from cyclohexane;

Regarding adipic acid the preparation of which is especially suited to the methods and apparatuses of this invention, general information may be found in a plethora of U.S. Patents, among other references. These, include, but are not limited to:

U.S. Pat. Nos. 2.223,493; 2,589,648; 2,285,914; 3,231, 608, 3,234,271; 3,361,806; 3,390,174; 3,530,185; 3,649, 685; 3,657,334; 3,957,876; 3,987,100; 4,032,569; 4,105, 856; 4,158,739 (glutaric acid); 4,263,453; 4,331,608; 4,606, 863; 4,902,827; 5,221,800; and 5,321,157.

Diacids (for example adipic acid, phthalic acid, isophthalic acid, terephthalic acid, and the like) or other suitable compounds may be reacted, according to well known to the art techniques, with a third reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by well known to the art techniques to form fibers.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

All explanations given hereinabove are to be considered as speculative and should not be construed as limiting the breadth of the claims.

What is claimed is:

1. A method of forming a polymer comprising the steps of:

(a) reacting a hydrocarbon with an oxidant at a first oxidation rate and at a first temperature in a first reaction zone, the first reaction zone having a first hold-up time; and (b) continuing reacting the hydrocarbon with the gaseous oxidant at a second oxidation rate and at a second temperature in a second reaction zone, the second reaction zone having a second hold-up time, the second temperature being lower than the first temperature, the first hold-up time to the second hold-up time being at a ratio lower than 1;

wherein the acid comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer selected from a group consisting of a polyester, a polyamide, a polyimide, and a polyamideimide.

2. A method as defined in claim 1, wherein the second temperature is 10% to 30% lower than the first temperature.

3. A method as defined in claim 1, further comprising a step of spinning the polymer into fibers.

4. A method as defined in claim 3 wherein the second temperature is 10% to 30% lower than the first temperature.

5. A method of forming a polymer comprising the steps of:

(a) reacting a hydrocarbon with an oxidant at a first oxidation rate and at a first temperature in a first reaction zone, the first reaction zone having a first hold-up time;

(b) continuing reacting the hydrocarbon with the gaseous oxidant at a second oxidation rate and at a second temperature in a second reaction zone, the second reaction zone having a second hold-up time, the second temperature being lower than the first temperature, the first hold-up time to the second hold-up time being at a ratio lower than 1; and (c) further comprising n–2 additional steps of continuing reacting the hydrocarbon with the gaseous oxidant at an nth oxidation rate in a nth reaction zone, the nth reaction zone having an nth hold-up time, at an nth temperature, the nth temperature being lower than a respective n–1 temperature in a respective n–1 reaction zone having an n–1 hold-up time, the n–1 hold-up time to the nth hold-up time being at a ratio lower than 1, n being an integer greater than 2;

wherein the acid comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer selected from a group consisting of a polyester, a polyamide, a polyimide, and a polyamideimide.

6. A method as defined in claim 5 wherein the second temperature is 10% to 30% lower than the first temperature.

7. A method as defined in claim 5, further comprising a step of spinning the polymer into fibers.

8. A method as defined in claim 7 wherein the second temperature is 10% to 30% lower than the first temperature.

9. A method of forming a polymer comprising the steps of:

(a) reacting a hydrocarbon with an oxidant at a first oxidation rate and at a first temperature in a first reaction zone, the first reaction zone having a first hold-up time; and (b) continuing reacting the hydrocarbon with the gaseous oxidant at a second oxidation rate and at a second temperature in a second reaction zone, the second reaction zone having a second hold-up time, the second temperature being lower than the first temperature the first hold-up time to the second hold-up time being at a ratio lower than 1;

wherein reacting the hydrocarbon is continued in step (a) until the hydrocarbon has attained a first conversion within a desired first conversion range, and the desired first conversion range is 1% to 10%;

wherein reacting the—hydrocarbon is continued in step (b) until the hydrocarbon has attained a second conversion within a desired second conversion range and the second desired conversion range is 5% to 50%; and wherein the acid comprises a compound selected from a group consisting of adipic acid, phthalic acid, isophthalic acid, and terephthalic acid, and the method farther comprises a step of reacting said intermediate oxidation product with a third reactant selected from a group consisting of a polyol, a polyamine, and a polyamide in a manner to form a polymer selected from a group consisting of a polyester, a polyamide, a polyimide, and a polyamideimide.

10. A method as defined in claim 9 wherein the second temperature is 10% to 30% lower than the first temperature.

11. A method as defined in claim 9, further comprising a step of spinning the polymer into fibers.

12. A method as defined in claim 11 wherein the second temperature is 10% to 30% lower than the first temperature.

\* \* \* \* \*